(12) United States Patent
Boese et al.

(10) Patent No.: US 7,508,913 B2
(45) Date of Patent: Mar. 24, 2009

(54) METHOD OR X-RAY DEVICE FOR CREATING A SERIES OF RECORDINGS OF MEDICAL X-RAY IMAGES OF A PATIENT WHO MIGHT POSSIBLY BE MOVING DURING THE RECORDING OF THE SERIES OF IMAGES

(75) Inventors: Jan Boese, Eckental (DE); Benno Heigl, Coburg (DE)

(73) Assignee: Siemens Aktiengesellschaft, Munich (DE)

( * ) Notice: Subject to any disclaimer, the term of this patent is extended or adjusted under 35 U.S.C. 154(b) by 342 days.

(21) Appl. No.: 11/478,097

(22) Filed: Jun. 29, 2006

(65) Prior Publication Data

US 2007/0003014 A1 Jan. 4, 2007

(30) Foreign Application Priority Data

Jun. 30, 2005 (DE) .................... 10 2005 030 609

(51) Int. Cl.
*H05G 1/10* (2006.01)
(52) U.S. Cl. ........................ 378/95; 378/62; 378/205
(58) Field of Classification Search ................ 378/205, 378/95, 62, 98.12, 108
See application file for complete search history.

(56) References Cited

U.S. PATENT DOCUMENTS

2003/0181809 A1 9/2003 Hall et al.
2004/0184583 A1* 9/2004 Nagamine et al. ........... 378/209
2005/0171420 A1 8/2005 Boese et al.
2005/0203373 A1 9/2005 Boese et al.

FOREIGN PATENT DOCUMENTS

DE          102 10 646 A1     10/2003
DE       10 2004 004 603 A1    8/2005
DE       10 2004 004 604 A1    9/2005

OTHER PUBLICATIONS

Graeme Patrick Penney, "Registration of Tomographic Images to X-ray Projections for Use in Image Guided Interventions", Chapter 3, Dissertation, Dec. 1999, King's College, London, pp. 1, 43, 64, 79-86.
Erik H.W. Meijering, Wiro J. Niessen and Max A. Viergever, "Retrospective Motion Correction in Digital Subtraction Angiography: A Review", IEEE Transactions on Medical Imaging, vol. 18, No. 1, Jan. 1999, pp. 1-21.
J.B. Antoine Maintz and Max A. Viergever, "A survey of medical image registration", Medical Image Analysis, 1998, vol. 2, No. 1, pp. 1-36.

* cited by examiner

*Primary Examiner*—Hoon Song

(57) ABSTRACT

The invention relates to a method or x-ray device for creating a series of two-dimensional medical x-ray images to be related to each other in an evaluation of a patient with initially a first x-ray image and subsequently a further x-ray image being created, a deviation caused by a patient movement in each case between the further x-ray image and an x-ray image of the previously created x-ray images being determined and a relative position between an x-ray emitter and x-ray detector used to create the x-ray images and the patient being set in the sense of compensating for the patient movement depending on the relevant deviation, in order to guarantee over the entire extent of the series recording x-ray images which can be related to each other with few errors in an inexpensive manner despite movement of the patient.

18 Claims, 4 Drawing Sheets

METHOD OR X-RAY DEVICE FOR CREATING A SERIES OF RECORDINGS OF MEDICAL X-RAY IMAGES OF A PATIENT WHO MIGHT POSSIBLY BE MOVING DURING THE RECORDING OF THE SERIES OF IMAGES

CROSS REFERENCE TO RELATED APPLICATIONS

This application claims priority of German application No. 10 2005 030 609.8 filed Jun. 30, 2005, which is incorporated by reference herein in its entirety.

1. Field of the Invention

The invention relates to a method or an x-ray device for creating a series of two-dimensional medical x-ray images, which are able to be related to each other in an evaluation, of a patient who may possibly be moving while the series of images is being recorded, especially for use with a series of images in accordance with a pathfinder technique.

2. Background of the Invention

There is provision in a number of x-ray examination methods for creating a series of two-dimensional x-ray images of a patient, which are then related to each other in an evaluation, with a x-ray images which coincide where possible being a pre-requisite for an evaluation with few errors. A possible movement of the patient during the course of the creation of the series of images adversely affects the coincidence of the x-ray images and thus makes it more difficult to correctly evaluate the x-ray images or even completely prevents this evaluation, so that the series recording, combined with the additional outlay in time and contrast means as well as with additional exposure to radiation of the patient, has to be partly or completely repeated.

In the evaluation the x-ray images of the series recording are for example related to each other by a physician looking at the x-ray images in turn or simultaneously in an assessment of the x-ray images of the series recording. The x-ray images can also be related to each other by a computer-based image processing by for example two of the x-ray images been processed into a new x-ray image, e.g. a differential image, by a computer.

An example of the above-mentioned x-ray examination method is what is known as the pathfinder technique, which is also referred to as road mapping. This technique is used in particular to visually track the current position of an x-ray-absorbent catheter navigated through a system of vessels of the patient on the basis of two-dimensional x-ray images recorded continuously during navigation and displayed immediately. Such an ongoing creation of x-ray images with its immediate display is also called fluoroscopy and the x-ray images are accordingly called fluoroscopy images. In order to enable the position of the catheter to be better detected relative to the vessel system, a contrast means is first injected before the introduction of the catheter into the vessel system and a first x-ray image of the vessel system is created as what is known as a mask image. This mask image presents the vessel system as a so-called roadmap for navigation. The x-ray images of the vessel system created in the course of the navigation without contrast means are subtracted from the mask image so that the catheter is detectable on any differential images created in this case as a light image in the vessel system which appears dark, whereas an image background of the mask image or of the relevant fluoroscopy image of no significance for the navigation is eliminated by its subtraction. In this example the relevant fluoroscopy image and the mask image are related to each other by the subtraction. The underlying technique of the subtraction of a first x-ray image of the vessel system with contrast means on the one hand and a further x-ray image of the vessel system without contrast means is also referred to as Digital Subtraction Angiography (DSA). Because of the patient movement between the creation of the fluoroscopy images, these no longer coincide with the mask image so that disturbing movement artifacts occur in the relevant differential images.

Three different methods are known for resolving the problem of possible movement of the patient while the series of images is being recorded.

A method called registration for subsequent image processing enables two x-ray images, e.g. the mask image and a relevant fluoroscopy image to be made to coincide after their creation. With the registration of two x-ray images, their relative position, e.g. on the basis of characteristic image elements, especially in the form of so-called landmarks, or on the basis of a degree of similarity, especially based on a gray value distribution of the two x-ray images, is determined and the two x-ray images are made to coincide by a transformation e.g. by a so-called rigid transformation comprising a relative rotation and/or a relative translation; these and other methods for registration are known per se from the article entitled "A survey of medical Image registration" by J. B. Antoine Maintz and Max A. Viergever (published in "Medical Image Analysis", 1998, Volume 2, Number 1, pages 1-36). Registration only makes it possible to compensate after the event for particular patient movements, such as the patient being displaced at right angles to an axis from an x-ray emitter to an x-ray detector for example which are used in each case to create the x-ray images; A rotation of the patient around an axis which is aligned at right angles to the above-mentioned axis can, because of the projection geometry, not be compensated for at all or only incompletely compensated for by registration.

In accordance with a second method, an undesired deviation in the x-ray images of the series recording, especially caused by a cyclic movement of the patient, can be avoided by a timed control of the creation of the x-ray images matched to the relevant cycle of the patient movement. Such cyclic patient movements are for example induced by the breathing or by the heartbeat of the patient. One disadvantage of this approach to a solution, which in the case of the cyclic movement in the form of breathing is known as breathing gating, lies in the fact that it can only be applied to cyclic patient movements.

In accordance with a third method the patient movement is avoided per se. This is done for example by the patient holding their breath during the series recording. A further option consists of restraining the patient during the series recording. Both the stated methods of this approach to a solution can however only partly prevent the patient from moving, especially during series recordings which take a long time.

SUMMARY OF THE INVENTION

The object of the invention is to guarantee, throughout the entire extent of a recording of a series of x-ray images of a patient, despite a possible movement of the patient, x-ray images able to be related to each other in a manner which requires little effort.

This object is achieved by a method or by an x-ray device according to the claims. Advantageous embodiments are the object of the associated subclaims in each case.

Through a setting of a relative position between an x-ray emitter and/or x-ray detector used to create the x-ray images on the one hand and the patient on the other hand in the sense of a compensation for the movement of the patient in each case, based on a deviation determined beforehand caused by a patient movement between a relevant further x-ray image of the series recording and one of the previously created x-ray images, x-ray images which can be related to each other with few errors can be obtained independently of the relevant patient movement, without in this case restricting the patient in any way in a uncomfortable manner for the patient e.g. by having them practice a special breathing technique or by restraining them; The setting of the relevant position between the x-ray emitter and/or the x-ray detector on the one hand and the patient on the other hand while the x-ray images are being recorded allows a compensation which is tailored more flexibly to the relevant patient movement than a subsequent registration of the two-dimensional x-ray images, which is restricted as a result of the projection geometry; advantageously an expensive subsequent post processing of the x-ray images after the creation of the series recording is avoided by the present invention.

In accordance with one embodiment of the invention there is provision for the deviation between the relevant further x-ray image and the first x-ray image of the series recording to be determined; the repeated referring back to the first x-ray image as the one of the previously created x-ray images simplifies the method. In the case of a series recording in accordance with the pathfinder technique the further x-ray image in each case corresponds to the current fluoroscopy image for which the deviation from a first x-ray image is determined in the form of a mask image; It should be taken into account when determining the deviation that the fluoroscopy image differs from the mask image not only through the patient movement but also through a contrast means or through a mapping of a catheter.

By iteratively repeating the steps in the method of creating the relevant further x-ray image, the determination of the deviation from the x-ray image previously created and the setting of the relative position between the x-ray emitter and/or the x-ray detector on the one hand and the patient on the other hand, in the sense of an optimization process related to the reduction of the deviation, a step-by-step approximation to a largely complete compensation for patient movement is possible.

In accordance with a further embodiment of the invention there is provision for executing the relevant method step for the optimization process as iterative intermediate steps with at least one x-ray image created on a trial basis, especially with a lower radiation dose than the relevant further x-ray image; this makes possible a selection of x-ray images which, because they completely compensate for patient movement, are especially well suited for the evaluation without restricting the optimization process in this case. The x-ray images created with the low radiation dose are especially suitable for continuing the optimization process without the patient being subjected to a high radiation load by a high number of iteration steps. If the x-ray images created with the lower radiation dose to not exhibit sufficient diagnostic quality they are not included for evaluation. The optimization process can also be undertaken during the interventional treatment, provided this requires a frequent and longer release of radiation with a lower dose (e.g. exposure during catheter positioning). In this case the additional exposure to radiation of the patient is avoidable for the optimization process.

The fact that the parameters for setting the relative position as a function of the quantitatively-determined deviation in the sense of a planned direct reduction of the deviation are computed before the adjustment means that the compensation for the patient movement combined with a low radiation dose is possible especially quickly; In this way, especially with an iterative reduction of the deviation, the number of the iteration steps required can be reduced.

The deviation can be determined especially simply in the form of a quantified rotation or quantified translation of the further x-ray image relative to one of the x-ray images created previously in each case; based on the deviation quantified in this form the direct reduction or the iterative reduction of the deviation succeeds particularly quickly. Based on this quantified deviation the patient movement in a plane at right angles to an axis through the x-ray emitter and the x-ray detector can be described by an angle of rotation and a translation vector in quantitative terms.

BRIEF DESCRIPTION OF THE DRAWINGS

The invention, as well as further advantageous embodiments of the invention in accordance with features of the subclaims, are explained in greater detail below with reference to schematic diagrams of exemplary embodiments in the drawing, without this restricting the invention to this exemplary embodiment in any way; The Figures show:

DETAILED DESCRIPTION OF THE INVENTION

Figure 1:
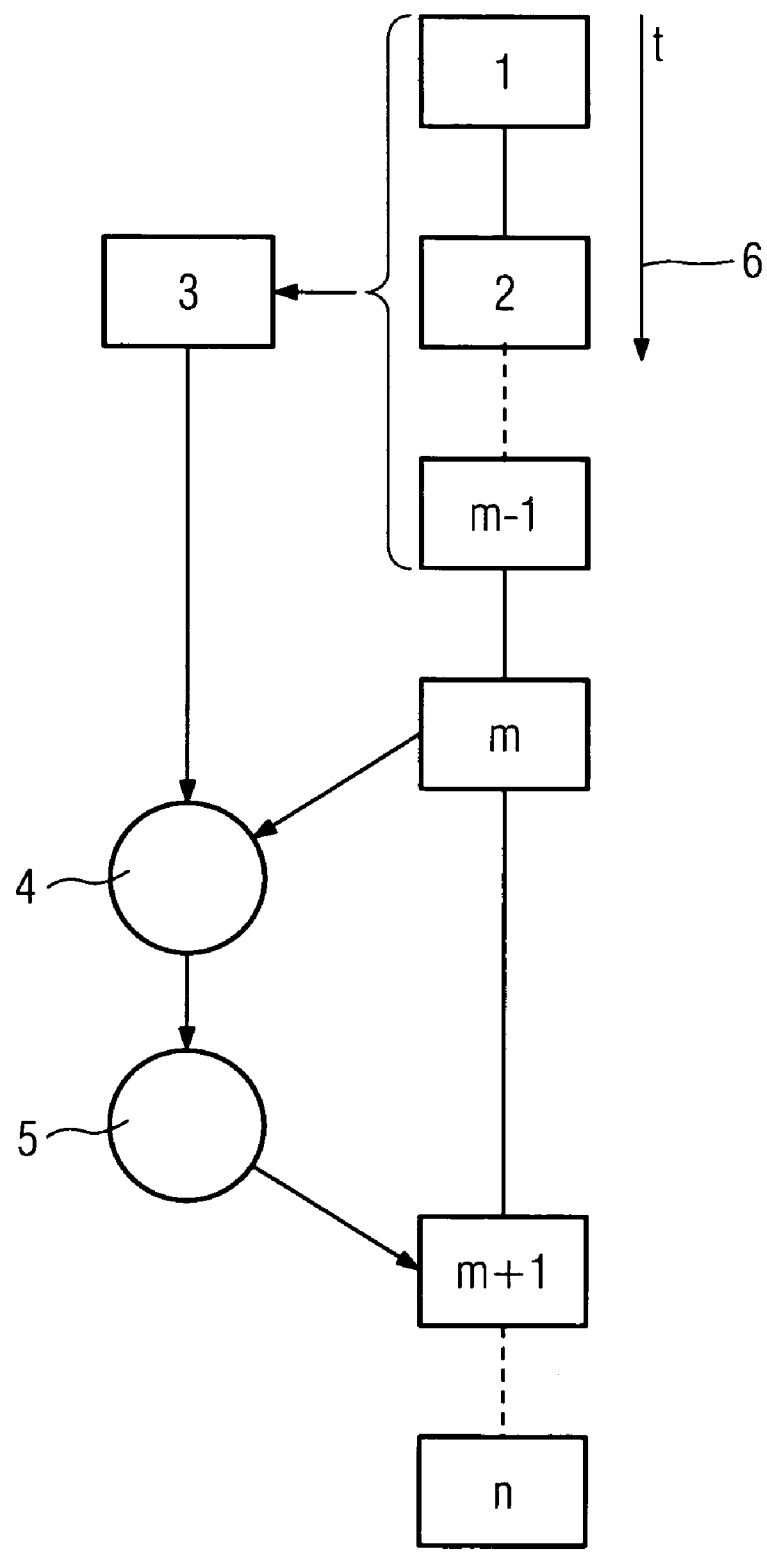
FIG. 1 an execution sequence over time of the inventive method based on a succession of x-ray images of a series recording.

FIG. 1 shows the execution sequence over time of the inventive method with reference to a succession of n two-dimensional medical x-ray images 1, 2, . . . , m−1, m, m+1, . . . , n with 1<m<n, which, in accordance with the relevant time of their creation, are arranged along a time axis 6 pointing in the direction of an increasing time t; Two further important method steps 4 and 5 for compensating for a patient movement are shown as examples, based on a relevant further x-ray image m, an x-ray image 3 of the previously created x-ray images 1, 2, . . . , m−1 in each case and an immediately following x-ray image m+1. The subsequent description relates to the point in time at which the further x-ray image m is created in each case, which consequently can also be designated as the current x-ray image in each case.

In accordance with the inventive method for creating a series recording of the x-ray images 1, 2, . . . , m−1, m, m+1, . . . , n of a patient who may possibly be moving during the course of the creation of the series recording, after the creation of the relevant further x-ray image m+1 following on from the first x-ray image 1 and before the creation of the next x-ray image m+1 directly following this image, there is provision that:

in method step 4 a deviation caused by a patient movement between the further x-ray image m on the one hand and the one x-ray image 3 of the x-ray images 1, 2, ..., m−1 created previously in each case on the other hand is automatically determined and in method step 5 the x-ray emitter and/or x-ray detector used for creation of the x-ray images 1, 2, ..., m−1, m, m+1, ..., n are automatically set in their relative position to the patient in the sense of a compensation for the patient movement depending on the relevant deviation.

With this method it is made possible to determine a patient movement after its occurrence on the basis of the relevant further x-ray image m and to compensate for it in a relevant directly following x-ray image m+1. On the one hand this prevents the errors caused by the movement of the patient accumulating in the course of the series recording of the x-ray images 1, 2, ..., m−1, m, m+1, ..., n, and on the other hand it guarantees that after a relevant patient movement subsides temporarily, a complete compensation for this patient movement is successful in the following x-ray images in each case.

Especially with series recordings of which x-ray images 2, ..., m−1, m, m+1, ..., n following on from the first x-ray image 1 are related in each case for evaluation to the first x-ray image 1, the first x-ray image 1 is expediently used as the one x-ray image 3 of the previously created x-ray images 1, 2, ..., m−1 in each case for determining the deviation. Accordingly in the application of the method to a catheter navigation in accordance with the pathfinder technique, the mask image which, in accordance with the pathfinder technique is the first x-ray image 1 of the series recording, is taken into consideration as the one x-ray image 3 of the relevant previously created x-ray images 1, 2, ..., m−1. The method avoids the catheter introduced into a vessel system appearing in a differential image from the relevant further x-ray image m and the mask image 1 at an incorrect location because of the patient movement, especially outside a vessel system shown on the differential image. Only with especially jerky patient movements or with a patient movement during an especially long period of time between two consecutive x-ray images of the series recording can an incorrect presentation temporarily occur, but this is subsequently rectified by the method however so that the navigation can be continued without any problems.

By an iterative repetition of the creation of a further x-ray image m in each case and the above-mentioned method steps 4 and 5 in the sense of an optimization process related to reducing the deviation an increasingly improved compensation for patient movement is made possible. In this case the previously mentioned method steps can be executed as iterative intermediate steps with at least one x-ray image created on a trial basis, especially with a lower radiation dose, than the relevant further x-ray image m, in order to only take account of such a further x-ray image m during the evaluation which can be correctly related to at least one of the remaining x-ray images 1, 2, ..., m−1, m+1, ..., n; X-ray images which, despite the application of the method exhibit a deviation which is too high, are by contrast not included for evaluation.

In the case of a deviation determined in the form of a quantified rotation or quantified translation of the relevant further x-ray image m relative to the one x-ray image 3 of the previously created x-ray images 1, 2, ..., m−1 in each case, the deviation quantified in this way can be reduced directly by a one-off execution of the aforementioned method steps 4 and 5. In this case the iterative optimization process for calculating a corresponding adjustment of the relative position can be undertaken beforehand with computer support.

An algorithm used for the optimization process can for example correspond to an algorithm for so-called 2D-3D registration of a two-dimensional x-ray image in relation to a three-dimensional x-ray image; Such algorithms for 2D-3D registration are known per se for example from Chapter 3 of the dissertation "Registration of Tomographic Images to x-ray Projections for Use in Images Guides Interventions" by G. P. Penney (December 1999, King's College London). For 2D-3D registration a projection with which a two-dimensional x-ray image is digitally reconstructed from the three-dimensional x-ray image is improved iteratively such that a deviation between an actual two-dimensional x-ray image and the digitally reconstructed x-ray image is reduced, with the algorithms which relate to the projection being able to be applied to setting the position in accordance with the previously described method.

The deviation is determined especially precisely by a comparison of the positions of the characteristic image elements, especially in the form of anatomical landmarks, in the relevant further x-ray image m with the corresponding positions of the same characteristic image elements in the one of the previously created x-ray images 1, 2, ..., m−1 in each case; these characteristic image elements can be detected automatically in a simple manner and compared in two different images.

Determining the deviation based on a degree of similarity of the relevant further x-ray image m by comparison of with the one x-ray image 3 of the previously created x-ray images 1, 2, ..., m−1 also succeeds especially precisely, with the reduction of the deviation corresponding to an increase in the degree of similarity; Examples of such a degree of similarity, for example based on a pixel intensity or a gray value distribution in the x-ray images, are already known from the aforementioned dissertation "Registration of Tomographic Images to x-ray Projections for Use in Images Guides Interventions" by G. P. Penney.

The two previously described methods for particularly precise determination of the deviation essentially correspond per se to known methods for intrinsic registration from the already mentioned article "A survey of medical Image registration" by J. B. Antoine Maintz and Max A. Viergever (see especially section on "intrinsic registration methods"); Comparable methods for registration are known from DE 102 10 646 A1. By contrast with the methods for registration given in these texts, instead of a computer-based alignment of the relevant x-ray images 3 and m, there is provision for the adjustment of the position of the x-ray emitter and/or x-ray detector relative to the patient.

A user monitoring the execution of the method can sometimes expediently stop the application of the method for the creation of the further x-ray image m if there is evidently no patient movement present so that in particular an unnecessary running of iterative optimization steps which may be associated with an additional radiation load imposed on the patient can be avoided. With an appropriate user entry the method steps 4 and 5 of determining the deviation or adjusting the relative position on creation of the relevant further x-ray image m are not executed.

Through an additional registration of the x-ray images after the creation of all x-ray images 1, 2, ..., m−1, m, m+1, ..., n of the series recording it is possible, despite the previously described setting of the relative position, to align x-ray images which do not completely coincide, and in this way to make a subsequent contribution to the compensation for patient movement; Methods for registration are known per se from the previously cited texts. A subsequent registration can be especially usefully applied if not all independent degrees of freedom which determine the position of the x-ray emitter and/or x-ray detector relative to the patient can be set with the relevant x-ray device or if the relative position cannot follow the movement of the patient sufficiently rapidly.

Figure 2:
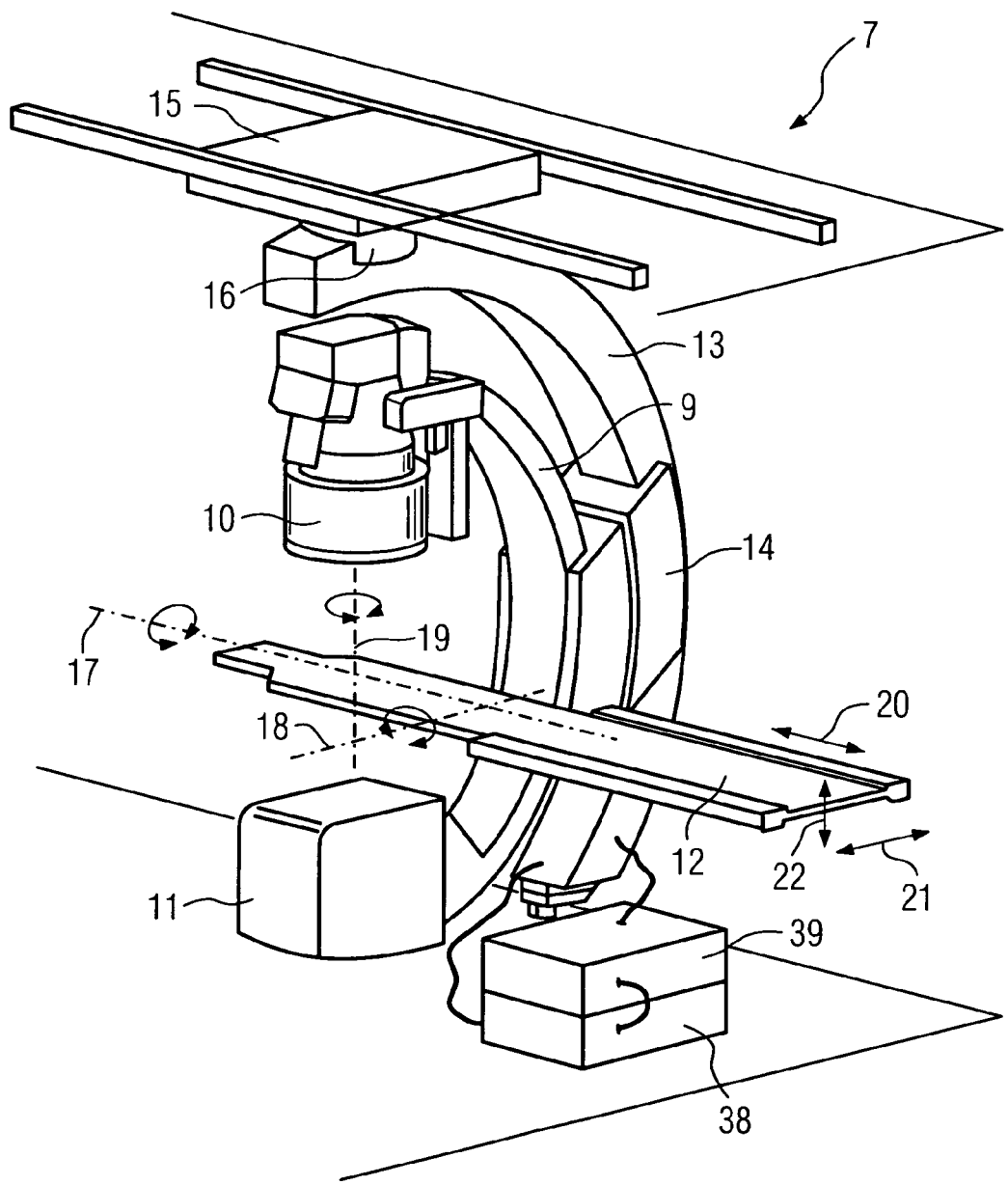
FIG. 2 in a perspective view, an x-ray device with a C-arm rotatable around three axes, and with a patient table moveable in three directions.

FIG. 2 shows in a perspective view an x-ray device 7 with an internal C-arm 9 for supporting an x-ray emitter 10 and an x-ray detector 11 as well as with a patient table 12 for a patient to be examined, who is not shown in the drawing. The inner C-arm is connected to an outer C-arm via an orbital lift 13 which allows a rotation of the inner C-arm around the orbital axis 17 and around the angulation axis 18. The outer C-arm is connected to a ceiling mount 15 via a universal joint 16 which allows a rotation of the outer C-arm 13 as well as the inner C-arm around a vertical axis 19. The patient table 12, for which the mount is not shown in order to make the drawing as easy to understand as possible can be adjusted by a translation in the two horizontal directions 20 and 21 as well as by a translation in the vertical direction 22. Through the previously described rotation and translation the relative position between the inner C-arm with the x-ray emitter 10 and/or the x-ray detector on the one hand and the patient on the other hand can be adjusted in all six possible degrees of freedom.

To determine the deviation caused by a patient movement between the relevant further x-ray image m and the one x-ray image 3 of the previously created x-ray images 1, 2, . . . , m−1, a computing means 38 is provided and to adjust the relative position between the x-ray emitter 10 and/or a the x-ray detector 11 on the one hand and the patient on the other hand, a control means 39 is provided.

Through a movement of the x-ray emitter 10 and/or of the x-ray detector 11 it is particularly easy to adjust the relative position since all components involved in its movement are known in their mechanical properties or these mechanical properties can be determined in advance. In addition, for the movement of the x-ray emitter 10 and/or the x-ray detector 11 it takes little effort to refer back to the known means, such as the C-arm stand 9, 13-16 for previously described rotation.

The fact that the movement of the x-ray emitter 10 and the x-ray detector 11 is undertaken with little effort by a translation and/or rotation in a rigid arrangement to each other, such as in this example in the form of an inner C-arm 9 with the x-ray emitter 10 and the x-ray detector 11, means that a separate movement control of the x-ray emitter 10 and the x-ray detector 11 is avoided without in this case restricting the options for compensating for movement of the patient.

The relative position between the x-ray emitter 10 and/or the x-ray detector 11 on the one hand and the patient on the other hand can however also expediently be undertaken by a translation, as shown in FIG. 2 and/or by rotation of the patient; In this exemplary embodiment the patient who is lying on a patient table 12 to create the series recording is to be moved by a translation of the patient table 12 in the three directions 20-22. Depending on the x-ray device used for executing the method, the relative position, as in this exemplary embodiment, can be set up through a combination of the movement of the x-ray emitter 10 and/or the x-ray detector 11 on the one hand and the patient or the patient table 12 on the other hand, with fewer than six degrees of freedom also being taken into account if necessary.

The case of the deviation determined in the form of a quantified rotation or quantified translation of the relevant further x-ray image m relative to one of the previously created x-ray images 1, 2, . . . , m−1 is explained with reference to FIG. 1. This deviation corresponds to a patient movement in a plane at right angles to an axis—in this exemplary embodiment identical to the vertical axis 19—through the x-ray emitter 10 and the x-ray detector 11. Such a patient movement can be compensated for by a rotation of the inner C-arm 9 around the vertical axis shown in this drawing or a translation of the patient table in a horizontal plane defined by the directions 20 and 21.

Figure 3:
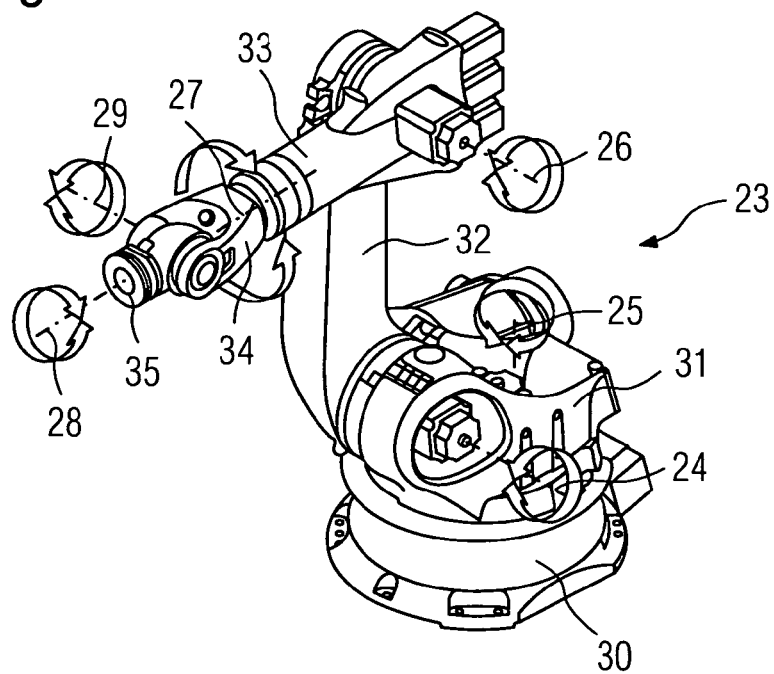
FIG. 3 in a perspective view, a robot featuring six axes of rotation with an attachment element.

FIG. 3 shows in a perspective view a robot 23 with six axes of rotation 24-29; this type of robot 23 is generally known from the prior art. Accommodated on a base frame 30 so that it can rotate around a first axis of rotation 24 is a carousel 31 on which a motion link 32 is mounted to pivot around a second pivot axis 25. An arm 33 is attached to the motion link 32 so that it can rotate around the third axis of rotation 26, with a hand 34 rotatable around a fourth axis of rotation 27 being accommodated on the end of the arm. The hand features an attachment element 35 which can be rotated around a fifth axis of rotation 28 and can be hinged around a sixth axis of rotation 29 running at right angles to this.

Figure 4:
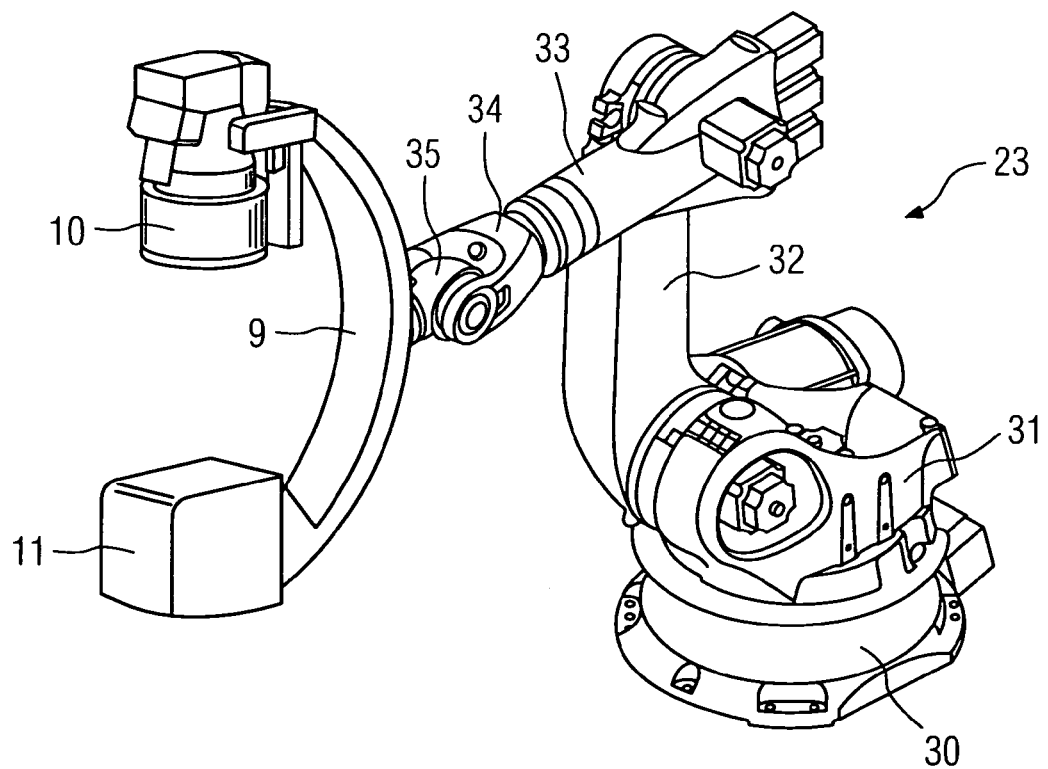
FIG. 4 the robot shown in FIG. 3 on the attachment element of which the C-arm with an x-ray emitter and an x-ray detector is arranged.

FIG. 4 shows robot 23 from FIG. 3 on the attachment element 35 of which is arranged the C-arm 9 already shown in FIG. 2 with the x-ray emitter 10 and the x-ray detector 11. With the aid of the robot 23 the C-arm can be adjusted in respect of its six basically possible degrees of freedom in its relative position to a patient not shown in this drawing.

In this exemplary embodiment the relative position between the x-ray emitter 10 and the x-ray detector 11 on the one hand and the patient on than other hand can be advantageously adjusted exclusively by the movement of the x-ray emitter 10 and the x-ray detector 11 arranged on the C-arm 9, so that a movement of the patient which is possibly stimulated by an acceleration occurring as he moves into an uncontrolled additional patient movement is avoided.

By using a robot 23 controllable in this exemplary embodiment in six degrees of freedom to move the C-arm 9 it is possible to rapidly adjust the x-ray emitter as well as the x-ray detector in their relative position to the patient, so that in this manner an especially delay-free compensation for patient movement can be achieved; in this case already available robots of the same type as the robot 23 illustrated in FIG. 3 can be employed at low-cost.

The patient can be accommodated during the series of recordings—similar to the way shown in FIG. 2—on a patient table 12. Alternatively, if a robot 23 which allows rapid movement is used, it is also possible to create a series of x-ray images 1, 2, . . . , m−1, m, m+1, . . . , n of the patient in an upright body position. This allows the patient to be examined in a natural load situation.

It is also conceivable to arrange the x-ray emitter and an x-ray detector on one robot 23 each and to move them separately.

Figure 5:
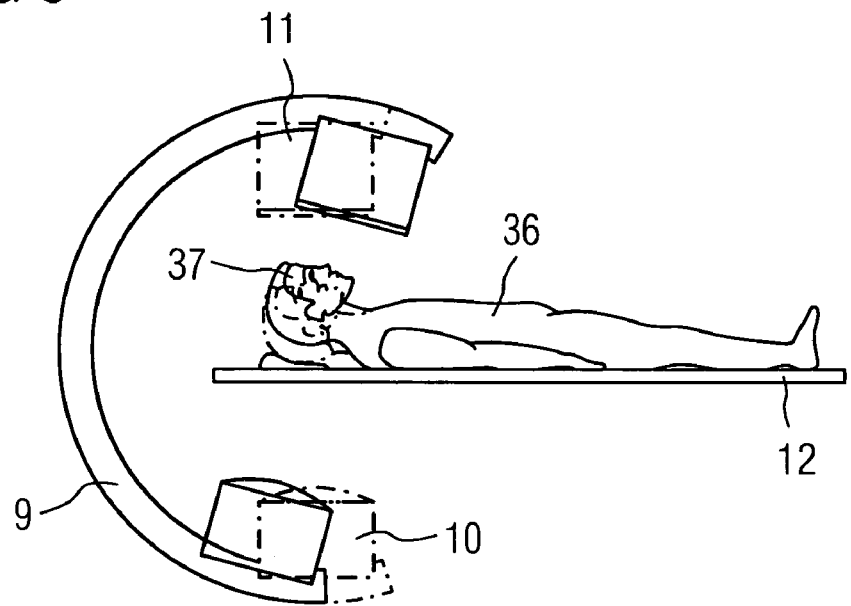
FIG. 5 in a side view, a patient who is moving on a patient bed as well as a C-arm which is adjusted in its position relative to the patient to compensate for patient movement.

FIG. 5 shows in a greatly simplified side view of the patient table 12 and the C-arm 9 with the x-ray emitter 10 as well as with the x-ray detector 11 as per FIG. 2, with a moving patient 36 lying on the patient table while a series of x-ray images 1, 2, . . . , $m^{-1}$, m, m+1, . . . , n of his head 37 are being created.

The patient 36 moves his head 37 from a starting position, which is shown by the dashed outline, vertically downwards to an end position, which is shown by the solid outline The deviation caused by this patient movement between an x-ray image m of the head 37 in the end position and a previously created x-ray image 3 is determined and subsequently the relative position between the C-arm with the x-ray emitter 10 and the x-ray detector 11 on the one hand and the head 37 of the patient 36 on the other hand depending on the deviation determined—in this exemplary embodiment—by a rotation of the C-arm in the counterclockwise direction from a start position which is shown by a dashed outline into an end position which is shown by a solid outline is adjusted so as to provide compensation for the patient movement for the subsequently created x-ray image m+1.

Figure 6:
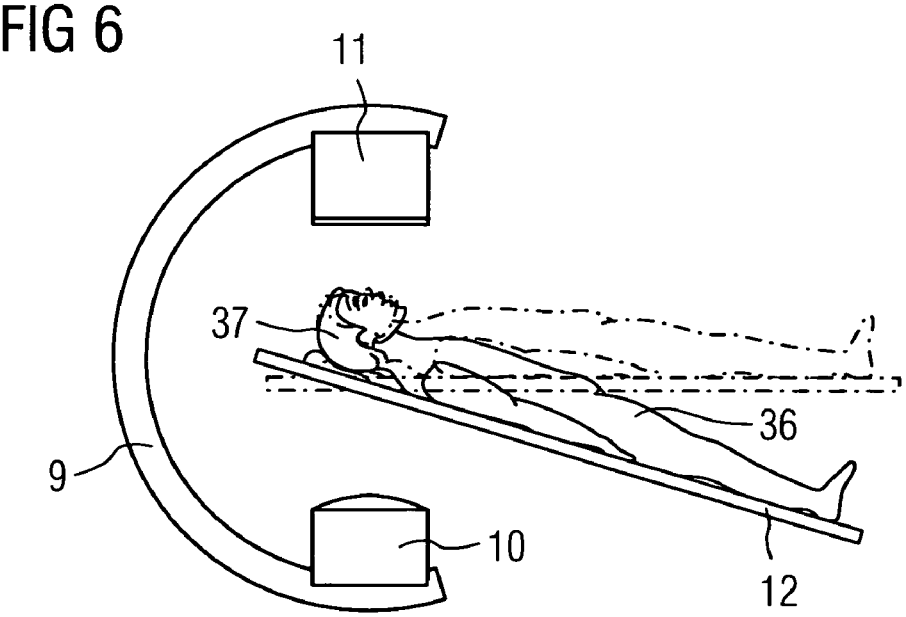
FIG. 6 the patient and the C-arm shown in FIG. 5, in which case, to compensate for movement of the patient, the patient table with the patient is adjusted in its position relative to the C-arm.

FIG. 6 like FIG. 5, also shows the patient table 12, the C-arm 9 and the patient 36 lying on the patient table 12. By contrast with FIG. 5 the patient movement is not compensated for by a rotation of the C-arm 9 but by a rotation of the patient table 12 in the clockwise direction from an initial position shown by a dashed outline into an end position shown by a solid outline.

The general point is made that a patient movement is taken to mean not only the movement of the patient 36 as a whole but also—as in the example described on the basis of FIGS. 5 and 6—the movement of a part of the body of the patient 36 or even the movement of an internal organ of the patient 36.

The invention can be summarized as follows: The invention relates to a method or x-ray device for creating a series of recordings and for an evaluation of two-dimensional medical x-ray images of a patient to be related one another, with initially a first x-ray image and subsequently a further x-ray image being created in each case, and then a deviation caused by a patient movement between the relevant further x-ray image and one of the previously created x-ray images being determined and subsequently the relative position in each case between an x-ray emitter and/or x-ray detector used for creating the x-ray images on the one hand and the patient on the other hand being adjusted depending on the relevant deviation, such that the patient movement is compensated for, in order to guarantee, over the entire extent of the series recording, x-ray images which can be related to each other with few errors in an inexpensive manner despite the movement of the patient.

The invention claimed is:

1. A method that compensates for movement of a patient on a patient table, comprising:
   recording a first set of x-ray images of a series with an x-ray emitter and an x-ray detector, wherein the series comprises a plurality of two-dimensional x-ray images taken in succession while the patient is lying on the patient table and which are related to each other;
   creating an additional x-ray image of the series with the x-ray emitter and the x-ray detector;
   determining a deviation caused by the movement of the patient between creating the additional x-ray image and recording one of the first set of x-ray images;
   setting a relative position between the x-ray emitter and the x-ray detector and the patient in order to compensate for the movement of the patient based on the determined deviation; and
   obtaining a further x-ray image of the series of two-dimensional x-ray images taken in succession with the set relative position, said obtaining providing the further x-ray image that compensates for the movement of the patient while on the patient table.

2. The method as claimed in claim 1, wherein the method is applied to the series of x-ray images with a pathfinder technique.

3. The method as claimed in claim 1, wherein the one of the first set of x-ray images that is used for determining the deviation is a first image of the first set of x-ray images.

4. The method as claimed in claim 1, wherein the creating, determining, and setting steps are repeated iteratively.

5. The method as claimed in claim 4, wherein the creating, determining, and setting steps are additionally executed as iterative intermediate steps with an x-ray image created as a trial image.

6. The method as claimed in claim 5, wherein the trial image is created with a lower radiation dose than the additional x-ray image.

7. The method as claimed in claim 1, wherein a parameter of a setting of the relative position is calculated based on the deviation in a planned direct reduction of the deviation before the setting.

8. The method as claimed in claim 1, wherein the deviation is determined by a quantified rotation or a quantified translation of the additional x-ray image relative to the one of the first set of x-ray images.

9. The method as claimed in claim 1, wherein the deviation is determined by a comparison of a position of a characteristic image element in the additional x-ray image with the one of the first set of x-ray images.

10. The method as claimed in claim 9, wherein the characteristic image element is an anatomical landmark.

11. The method as claimed in claim 1, wherein the deviation is determined based on a degree of similarity by a comparison of the additional x-ray image with the one of the first set of x-ray images.

12. The method as claimed in claim 11, wherein the degree of similarity is a pixel intensity or a gray value distribution in the series of the x-ray images.

13. The method as claimed in claim 1, wherein the setting step is stopped by a medical x-ray operator.

14. The method as claimed in claim 1, wherein the relative position is set by a movement of the x-ray emitter and the x-ray detector.

15. The method as claimed in claim 14, wherein the movement is a translation or a rotation of a rigid arrangement of the x-ray emitter and the x-ray detector relative to the patient.

16. The method as claimed in claim 15, wherein the rigid arrangement is a C-arm and is moved by a robot controllable in six degrees of a freedom.

17. The method as claimed in claim 1, wherein the relative position is set by a translation or a rotation of a patient table with the patient.

18. The method as claimed in claim 1, wherein a registration of the series of x-ray images is undertaken after the series has been created.

* * * * *